(12) United States Patent
Kawaguchi et al.

(10) Patent No.: US 6,422,081 B1
(45) Date of Patent: Jul. 23, 2002

(54) ULTRASONIC SOUND VELOCITY MEASURING METHOD AND ITS APPARATUS

(75) Inventors: Kenji Kawaguchi; Masanori Yasuda, both of Kyoto (JP)

(73) Assignee: Kyoto Electronics Manufacturing Co., Ltd. (JP)

( * ) Notice: Subject to any disclaimer, the term of this patent is extended or adjusted under 35 U.S.C. 154(b) by 122 days.

(21) Appl. No.: 09/588,698

(22) Filed: Jun. 7, 2000

(30) Foreign Application Priority Data

Jun. 7, 1999 (JP) .......................................... 11-159595

(51) Int. Cl.[7] ............................................. G01N 29/02
(52) U.S. Cl. ............................. 73/602; 73/597; 73/609
(58) Field of Search ........................... 73/602, 597, 598, 73/629, 24.06, 54.24, 54.41, 61.45, 61.49, 61.75, 61.79, 64.42, 609

(56) References Cited

U.S. PATENT DOCUMENTS

| | | | | |
|---|---|---|---|---|
| 3,992,679 A | * | 11/1976 | Isono | 331/1 R |
| 4,492,117 A | * | 1/1985 | Chubachi | 73/597 |
| 5,125,273 A | * | 6/1992 | Negita | 73/597 |
| 5,214,955 A | * | 6/1993 | Yost et al. | 73/61.75 |
| 5,557,047 A | * | 9/1996 | Koide | 73/597 |
| 5,856,622 A | * | 1/1999 | Yamamoto | 73/861.28 |

* cited by examiner

Primary Examiner—Hezron Williams
Assistant Examiner—Jacques M. Saint-Surin
(74) Attorney, Agent, or Firm—Ronald E. Greigg

(57) ABSTRACT

The invention relates to a method and apparatus for measuring a speed of an ultrasonic wave propagated in a sample, even if there are bubbles in a sample. And it presupposes an ultrasonic speed measuring method for seeking a sonic speed in a sample in accordance with the propagation time of an ultrasonic wave propagated between an ultrasonic transmitter and an ultrasonic receiver by transmitting the ultrasonic wave from the ultrasonic transmitter. The apparatus of this invention is arranged that continuous oscillating waves are oscillated synchronizing the phase only with the receipt timing of at least one of receiving waves received by the ultrasonic receiver at every transmitting waves, and according to the continuous oscillating waves it is possible to measure the period of pulses oscillated by the local oscillator for determining the transmit timing.

6 Claims, 7 Drawing Sheets

ULTRASONIC SOUND VELOCITY MEASURING METHOD AND ITS APPARATUS

BACKGROUND OF THE INVENTION

1. Field of the Invention

This invention relates to an ultrasonic speed meter and an ultrasonic speed measuring method, and more specifically to an apparatus and method for measuring the sonic speed propagated through a sample including bubbles.

2. Background

FIG. 4 is a block diagram showing an ultrasonic transmitter-receiver installed in an ultrasonic speed meter. A reflection board 2b is provided at a specific position distant from the ultrasonic transmitter-receiver 2a, and the space between the ultrasonic transmitter-receiver 2a and the reflection board 2b is filled with the sample. Under such arrangement, ultrasonic waves sent from oscillating elements (not shown) provided on the ultrasonic transmitter-receiver 2a are received by receiving elements (not shown) provided on the ultrasonic transmitter-receiver 2a and then converted to electric signals.

When an ultrasonic wave is propagated through a sample, the ultrasonic speed meter can seek the sonic speed c by using a propagation period T and a propagation distance L in accordance with the following equation: c=L/T. By using the sonic speed c, it is possible to calculate a physical value of the sample, for example, the density.

The overlap method and the sing-around method are generally known as the method for seeking the propagation period T with accuracy.

The overlap method is configured as shown in FIG. 5 and FIG. 6. Specifically, square waves Ws outputted from a square wave oscillator 101 are divided into divided waves Ds by a divider 107. The divided waves Ds are inputted to a pulsar 102. The pulsar 102 generates drive pulses Pd, which are inputted to an ultrasonic transmitter-receiver 103. In addition, the receiving wave obtained here is inputted to an oscilloscope 105 via an amplifier 104.

On the other hand, the oscilloscope 105 is driven by the output of the square wave oscillator 101. Therefore, when the period of the square wave Ws driving the oscilloscope 105 matches with that of the reflected wave Sr obtained from the ultrasonic transmitter-receiver 103, the monitor of the oscilloscope gets static and the period at that time becomes the period T.

In the above method, since adjusting the oscillating frequency of the square wave oscillator 101 by hand can keep the displaying of the oscilloscope static, there is a problem that it is impossible to perform the automatic measurement.

The sing-around method is configured as shown in FIG. 7. Specifically, a pulsar 201 oscillates drive pulses according to the input of starting trigger, and said drive pulses are inputted to the ultrasonic transmitter-receiver 103. According to the receiving waves from the ultrasonic transmitter-receiver 103, a pulse forming unit 203 forms a new trigger, and said new trigger is inputted to the pulsar 201. In this case, the pulses formed by the pulse forming unit 203 are inputted into a frequency counter 204, and the frequency counter 204 can calculate the period T according to the counted value that the frequency counter 204 has obtained for a specific time.

The prescribed method is easy to be subjected to the influence of the configuration of external circuits and etc. The obtained period T can be represented by a additional value of a true period $\tau_o$ and the circuit delay time $\tau_e$.

Accordingly an ultrasonic speed meter disclosed in Japanese Laid-open Publication No. H06-235721 is arranged as shown in FIG. 8 that the accurate propagation period T can be measured automatically by using a local oscillator generating continuous waves First, after receiving the receiving wave at least twice from the ultrasonic transmitter-receiver 103 in accordance with the drive pulses oscillated at a specific time by a drive pulse oscillating circuit 301, dividing means 302 divides the first receiving wave and the second receiving wave. And the drive pulse oscillating circuit 301 generates next drive pulse based on the first receiving wave ① while the local oscillator 304 oscillates a pulse corresponding to the propagation period T based on the second receiving wave ②. According to thus generated pulses, a time counting circuit 305 may count the propagation period T. And moreover, while the pulse corresponding to the first receiving wave ① extracted from the output of the local oscillator 304 is made to be a reference pulse of the local oscillator 304, the extracted pulse corresponding to the second receiving wave ② is made to be a reference pulse of the drive pulse oscillating circuit 301.

Since the ultrasonic speed meter disclosed in Japanese Laid-open Publication No. H06-235721 needs a minimum of two receiving waves every one transmitting wave (a drive pulse), there is a problem that a sufficient measurement result cannot be obtained in case of a sample including bubbles. This is to say; the ultrasonic speed meter cannot obtain two or more receiving waves every transmitting wave because the ultrasonic wave is attenuated by the influence of the bubbles, with the result that the continuous oscillation is disturbed and the measurements scatter widely.

SUMMARY OF THE INVENTION

Considering the problems in the prior arts described above, the present invention has an object to provide an ultrasonic speed meter and ultrasonic speed measuring method, even if there arc bubbles in a sample, that is able to measure the sonic speed of the ultrasonic wave with high accuracy.

In order to achieve the above object, the invention adopts the following means. And the invention presupposes an ultrasonic speed measuring method an shown in FIG. 1 that an ultrasonic wave transmitted from an ultrasonic transmitter is propagated between the ultrasonic transmitter and an ultrasonic receiver, and according to a propagation time of the propagating ultrasonic wave the sonic speed can be sought.

In the ultrasonic speed measuring method, continuous oscillating waves may be oscillated synchronizing a phase with the timing of receiving at least one receiving wave that the ultrasonic receiver has received according to a plural times transmissions, and it is arranged to measure the period of pulses oscillated by a local oscillator for determining the transmission timing based on the delayed receiving wave. Specifically, after a receiving wave received by an ultrasonic receiver is delayed for a specific period, continuous oscillating waves may be oscillated synchronizing the phase only with the receipt timing of the delayed receiving wave. And according to the continuous oscillating waves, it is arranged to measure the period of pulses oscillated by a local oscillator for determining the transmission timing. Therefore the ultrasonic speed can be sought by using the propagation time based on the period thus measured.

As a result of the above configuration, it is possible to perform the phase synchronization only on the received signals so that the stable measurement can be carried out without the influence of bubbles.

BRIEF DESCRIPTION OF THE INVENTION

REFERRED EMBODIMENTS OF THE INVENTION

Figure 1:
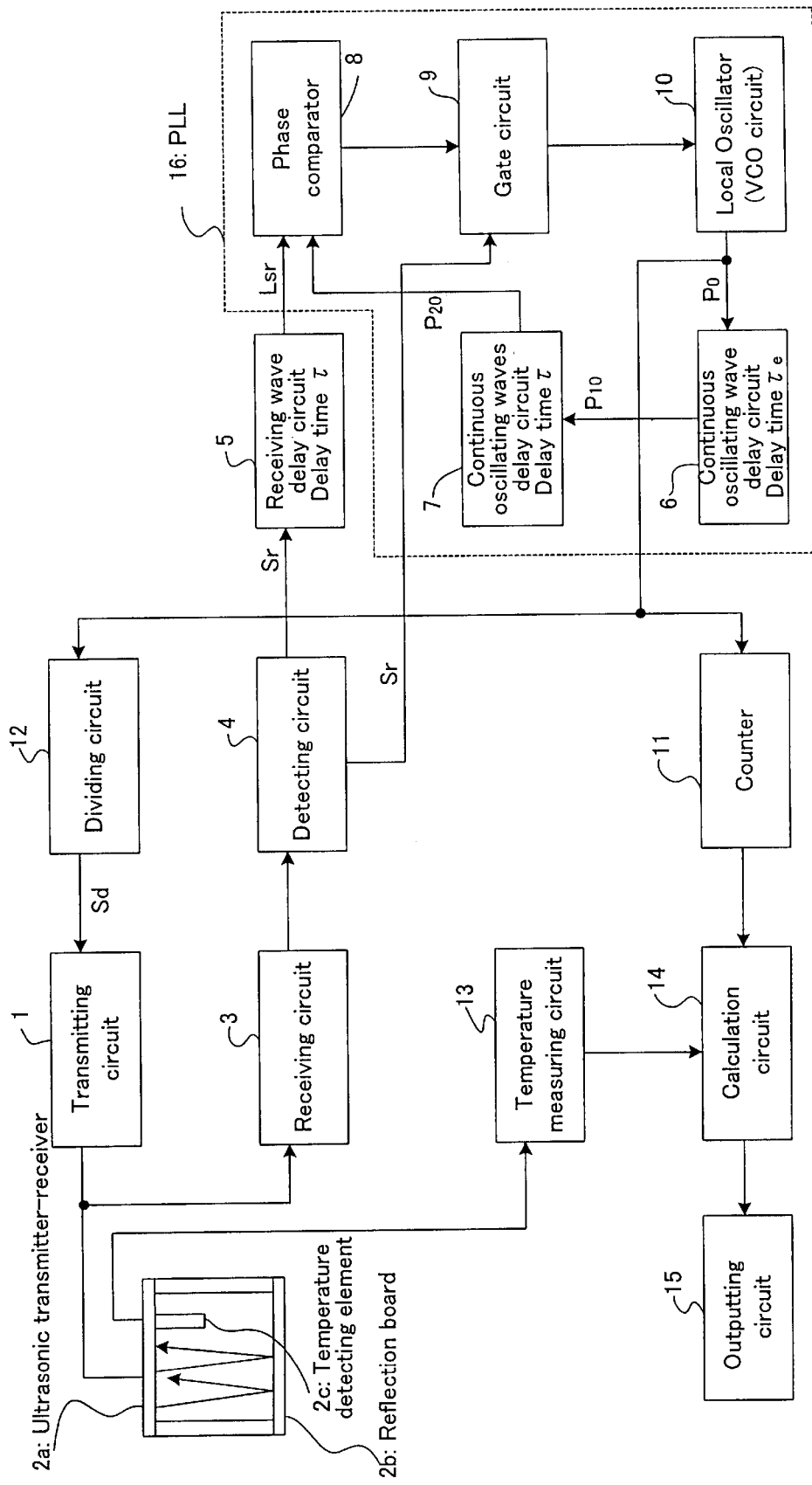
FIG. 1 is a block diagram showing an ultrasonic speed meter adopting the invention.

The preferred embodiments of this invention are discussed in details hereafter referring to the drawings.

Figure 2:
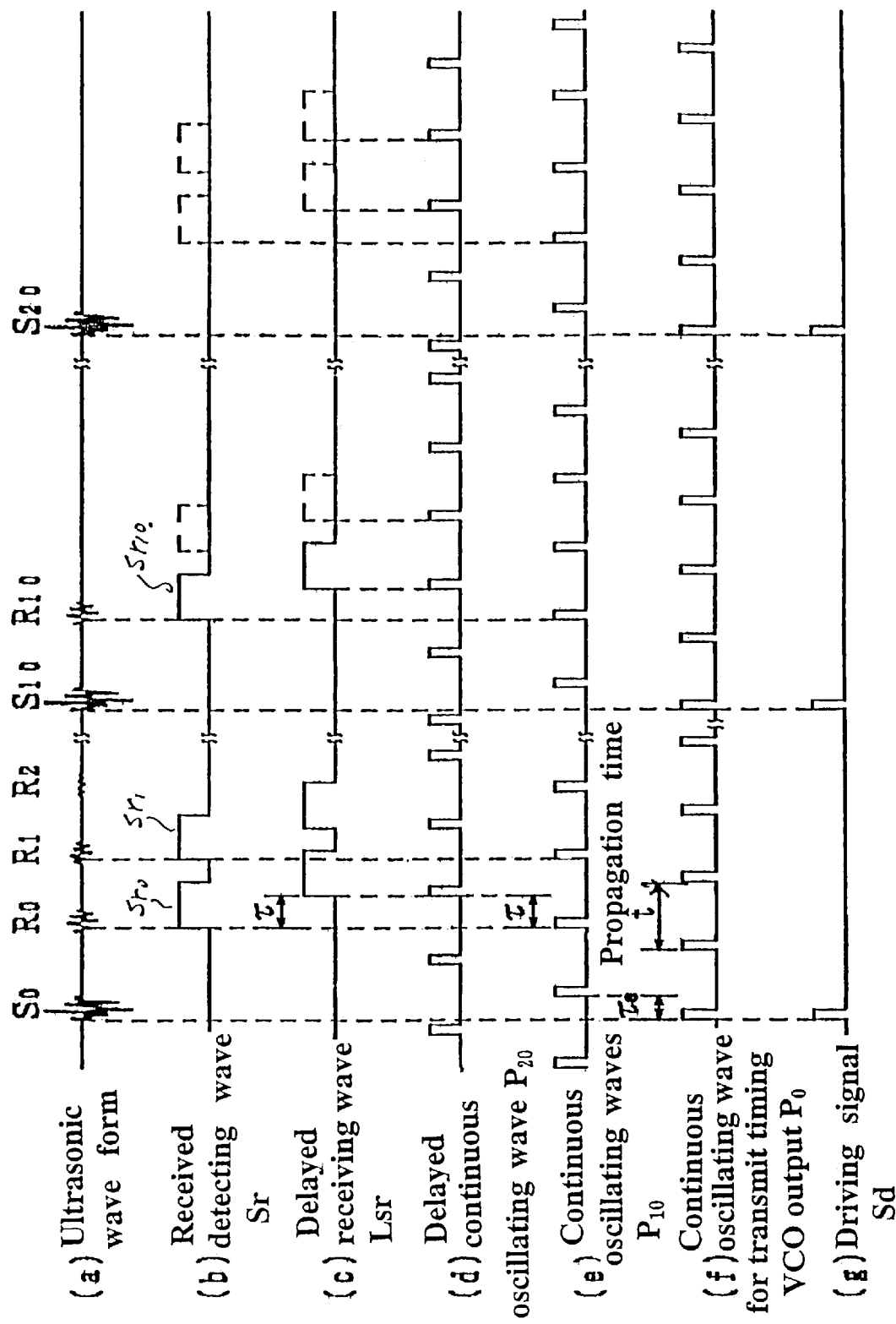
FIG. 2 is a timing chart of the invention.

FIG. 1 is a block diagram showing an ultrasonic speed meter adopting the invention, and FIG. 2 is a timing chart thereof.

The space between a transmitter-receiver 2a and a reflection board 2b is filled with a sample, said transmitter-receiver 2a comprising a transmitter and a receiver for the ultrasonic wave. The transmitter-receiver 2a oscillates an ultrasonic wave S0, S10 . . . as shown in FIG. 2(a) according to the driving of the transmitting circuit 1. The ultrasonic wave (which is called a "transmitting wave" hereafter) S0, S10 . . . is reflected on the reflection board 2b provided at a specific position distant from the ultrasonic transmitter-receiver 2a, and then turns back to the ultrasonic transmitter-receiver 2a. Moreover, the transmitting wave is reflected on the ultrasonic transmitter-receiver 2a again. Thereby a multiple reflected wave (R0, R1 . . . ), (R10, R11 . . . ) is generated between the ultrasonic transmitter-receiver 2a and the reflection board 2b, as shown in FIG. 2(a).

After the multiple reflected waves are received by the ultrasonic transmitter-receiver 2a and amplified by the receiving circuit 3, detecting circuit 4 forms said waves in a square waveform. Thereby it is possible to obtain a received detecting wave Sr as shown in FIG. 2(b). The detecting circuit 4 may adopt as a receiving wave only a reflected wave that is over the level of specific intensity. For instance, as shown in FIG. 2, the detecting circuit 4 adopts as the receiving waves both the first reflected wave R0 and the second reflected wave R10 for the first oscillating wave S0, and the received detecting wave $Sr_o$, $Sr_l$, $Sr_m$ corresponding to the first reflected wave R10 for the second oscillating wave S10, because those are over the specific level. But since the entire reflected waves corresponding to the third oscillating wave S20 is under the specific level, either of them cannot be received.

As a cause that the reflected wave has changed below the specific level as mentioned above comes from obstacles generated in a sample, for example, bubbles. When the receiving wave cannot be detected as mentioned above, if a PLL circuit that will be described later is started up, the result of the measurement could go wrong. Therefore, the invention adopts a configuration that only the reflected wave, which is detected over the specific level of the intensity, may be adopted as a transmitting wave.

Specifically, the received detecting wave Sr may be delayed only a specific time τ by a receiving wave delay circuit 5 (the first delay circuit), so that it is possible to obtain a delayed receiving wave LSr as shown in FIG. 2(c). The delayed receiving wave LSr is inputted as a comparing signal to a phase comparator 8 of the PLL 16. On the other hand, the oscillating wave $P_0$ (continuous oscillating waves for the transmit timing) outputted from the local oscillator 10 of the PLL 16 is delayed $τ_e$ by a delay circuit 6 and also delayed the specific time τ by a delay circuit 7 (the second delay circuit=the delay circuit 6+the delay circuit 7), so that said wave changes to delayed continuous oscillating waves $P_{20}$, which are inputted as the reference wave to the phase comparator 8. Thereby, the rising phase of the delayed receiving wave LSr is compared with the rising phase of the delayed continuous oscillating waves $P_{20}$, and then the compared result is outputted from the phase comparator 8.

The output of the detecting circuit 4 is inputted as a control signal to a gate circuit 9 of the PLL 16. Accordingly, the phase comparator 8 compares the phase difference based on only the transmit timings of the received detecting wave Sr, and the above compared result (i.e. the difference between the rising phase of the delayed receiving wave LSr and the rising phase of the delayed continuous oscillating waves $P_{20}$) may be reflected in the oscillating frequency of the local oscillator 10 passing through the gate circuit 9. Specifically, in case the received detecting wave Sr cannot be obtained by the influence of bubbles, since the gate circuit 9 is closed, the compared result of the phase comparator 8 cannot be reflected. Accordingly, the period τ described above is equivalent to a time required to acquire the above-mentioned compared result.

In the prescribed configuration, if there is at least one time reflected wave corresponding to plural oscillating waves S0, S10 . . . oscillated at specific time intervals, it is possible to obtain the continuous oscillating waves $P_0$ which is synchronized with the time intervals of the multiple reflection. The counter 11 measures the period of the continuous oscillating waves $P_0$. The calculation circuit 14 calculates the sonic speed in accordance with thus measured period and the temperature value measured by the temperature measurement circuit 13, and outputs the result to the outputting means 15 such as a printer or a display. The example in FIG. 2 shows that the reflected wave R0, R1 . . . is received corresponding to the oscillating wave S0, while the reflected wave R10 is received corresponding to the oscillating wave S10. In addition, the drawing also shows that no reflected wave is received corresponding to the oscillating wave S20.

When the receiving wave cannot be detected because of the obstacles such as bubbles in the sample, if the result comparing the delayed continuous oscillating waves $P_{20}$ and the non-generated delayed receiving wave LSr is reflected in the oscillating frequency of the local oscillator 10, the objective frequency cannot be obtained. But if the detecting wave is delayed the specific time τ, since the control signal based on the existence of the receiving wave is inputted from the detecting circuit 4 (the signal having the timing before the delay) to the gate circuit 9, it is possible to control the opening and close of the gate circuit 9. And when the reflected wave cannot be detected, since the gate circuit 9 is kept close, the result comparing the delayed continuous oscillating waves $P_{20}$ and the non-generated delayed receiving wave LSr is not reflected in the oscillating frequency of the local oscillator 10.

Under the physical and electrical conditions, in case the time from oscillating the ultrasonic wave to receiving the first reflected wave R0, R10 . . . is compared with the time from receiving the first reflected wave R0, R10 . . . to receiving the reflected wave from the second time downward, the former is a little longer ($\tau_e$). Therefore the delayed period of the continuous oscillating waves delay circuit 6 is corresponding to the $\tau_e$. The dividing circuit 12 forms a driving signal Sd by using the rising phase of the continuous oscillating waves $P_0$ which is before being delayed the time $\tau_e$. That is to say, the timing of the driving signal is faster by $\tau_e$ than the continuous oscillating waves $P_{10}$ synchronizing with the non-delayed received detecting wave Sr.

The $\tau_o$ becomes a unique value for the apparatus because it depends on not the kind of the sample but the electrical and physical factors such as a necessary elements for oscillating the ultrasonic wave. Therefore the $\tau_e$ should be adjusted in order that every apparatus can oscillate the continuous oscillating waves in most stable.

The dividing ratio of the dividing circuit 12 depends on the kind of sample, therefore it should be arranged that the next transmitting wave may not be oscillated until plural receiving waves corresponding to a specific sending wave is attenuated sufficiently.

Figure 3:
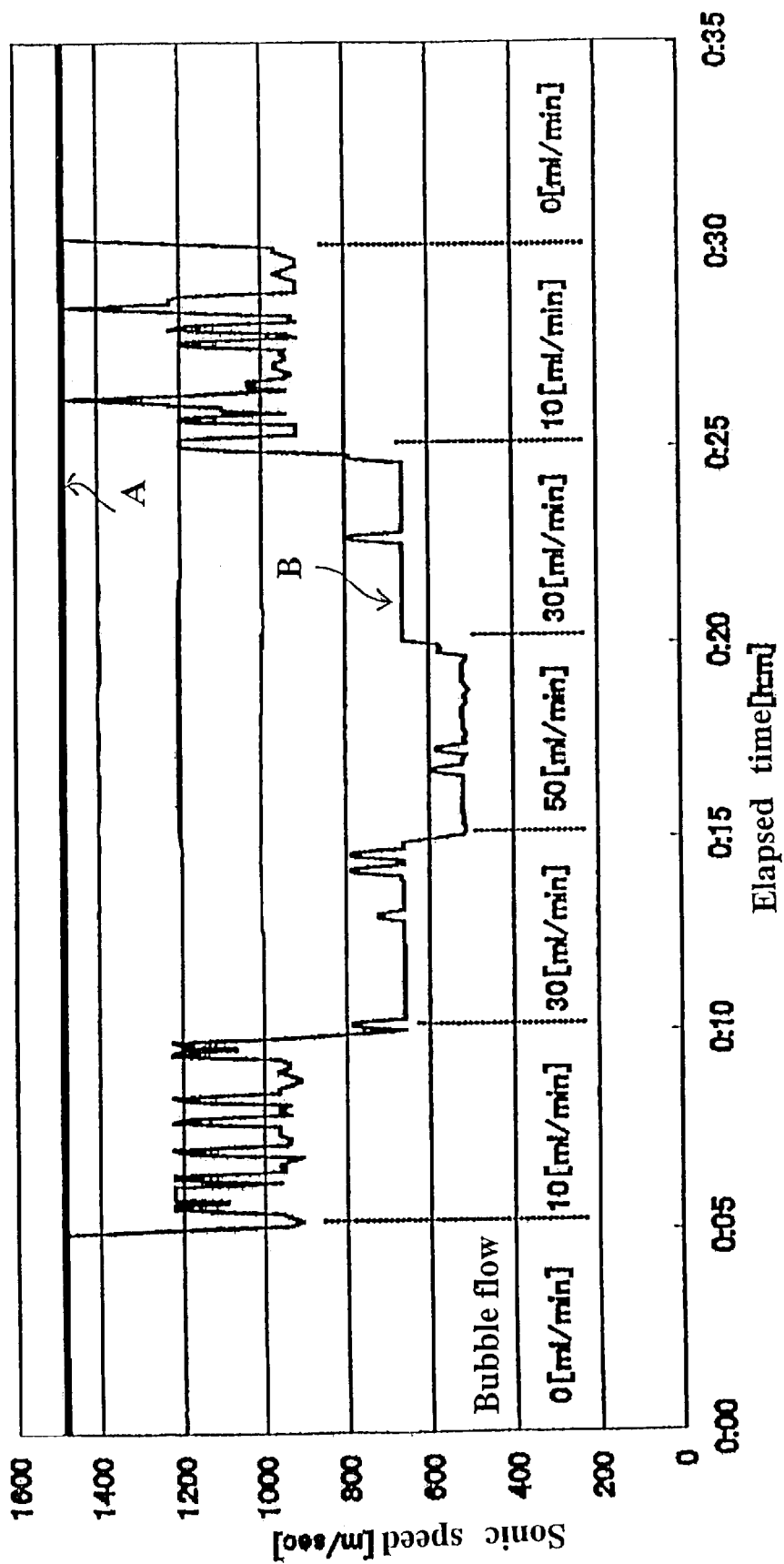
FIG. 3 is a diagram indicating the measurement results by both the invention and the conventional method.
Figure 4:
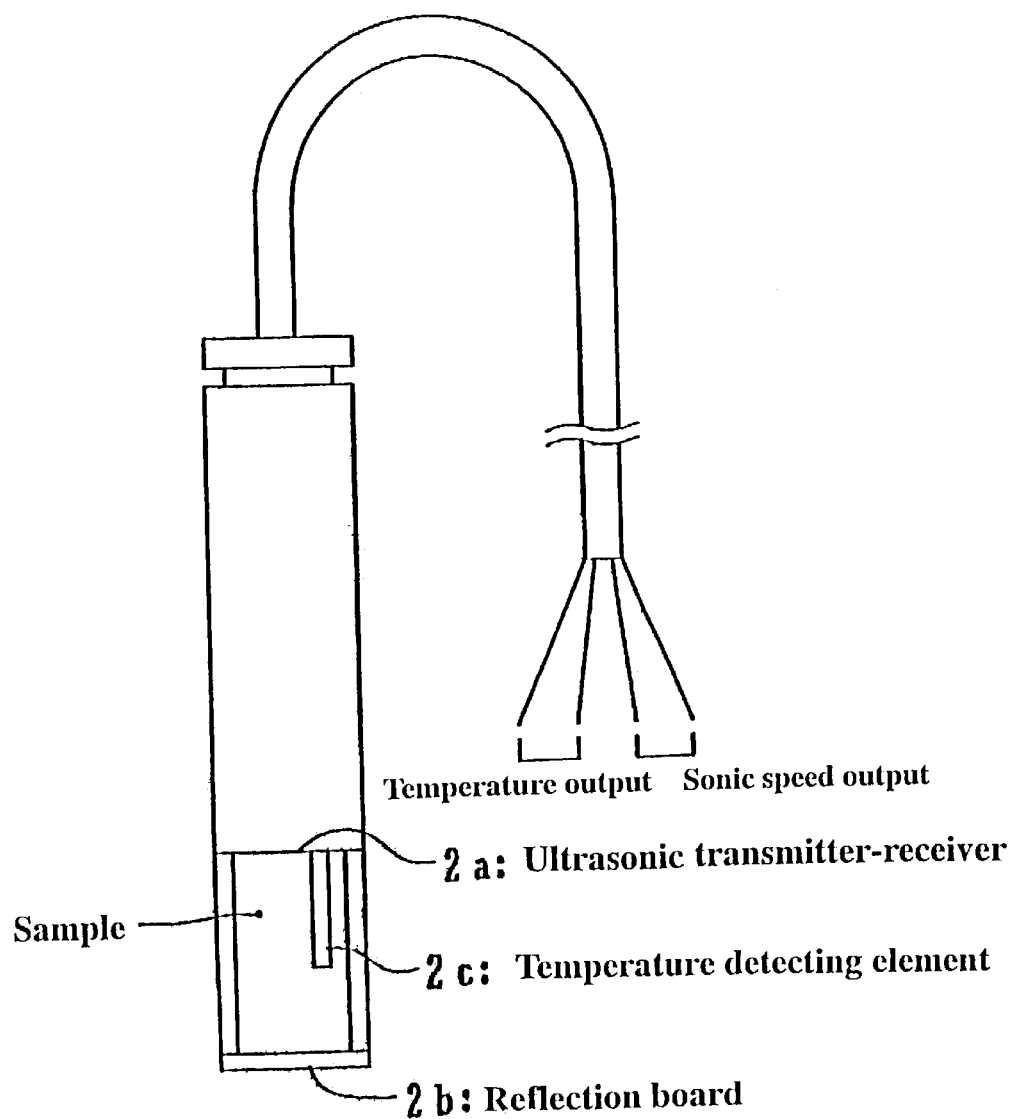
FIG. 4 is an outline view showing an ultrasonic transmitter-receiver installed in the ultrasonic speed meter.
Figure 5:
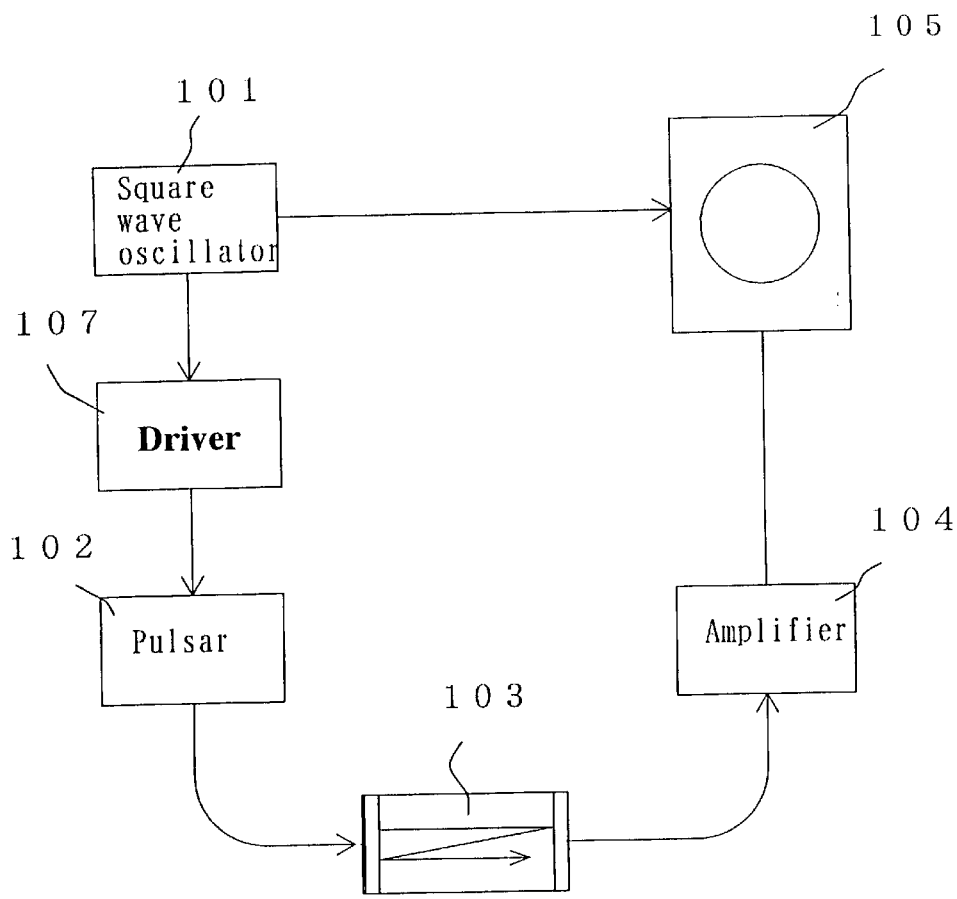
FIG. 5 is a conceptual view of the overlap method of the conventional technique.
Figure 6:
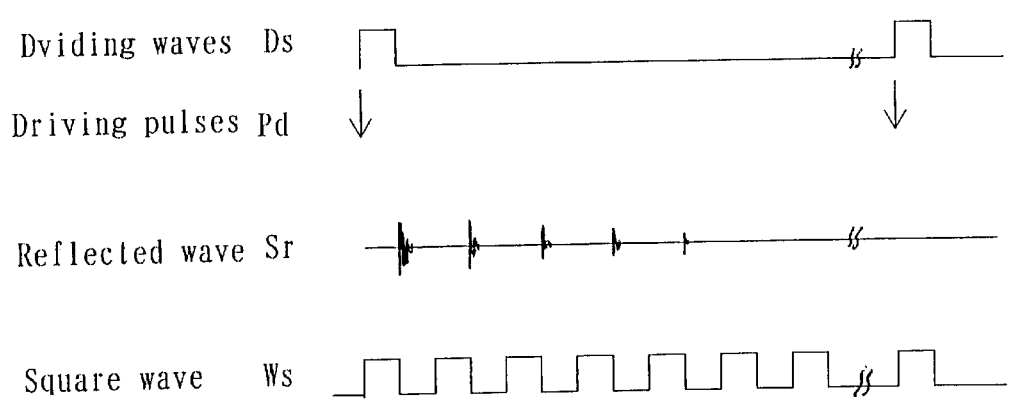
FIG. 6 is a time chart of the overlap method of the conventional technique.
Figure 7:
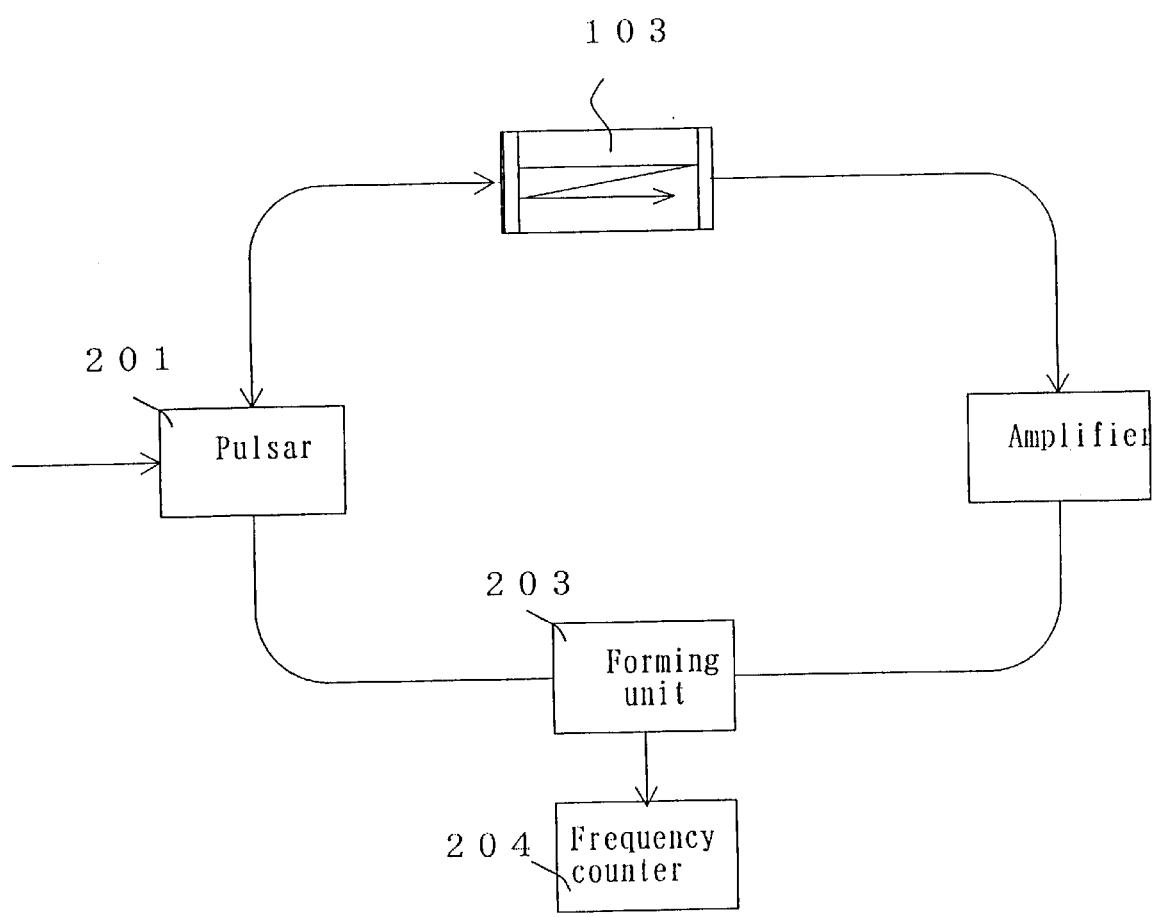
FIG. 7 is a conceptual view of the sing-around method of the conventional technique.
Figure 8:
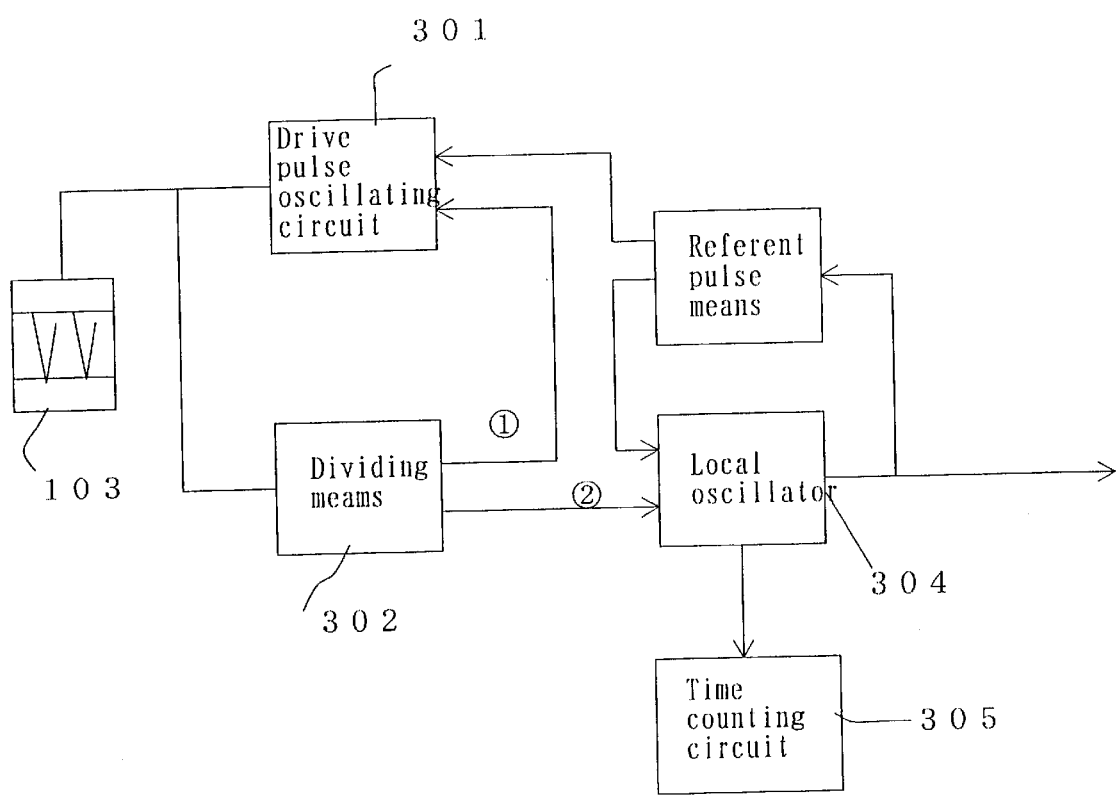
FIG. 8 is a conceptual view of the other conventional technique.

FIG. 3 shows the result that the sonic speed propagated in the ion-exchange solution at 20° C., in which the bubble flow changes every 5 minutes, is measured by both the present invention and the conventional method (the sing-around method). The bubbles passes through a tube nozzle of φ6 bubbling with air. The measurement result A based on this invention indicates a stable result regardless of more or less of the bubbles, while the measurement result B based on the conventional method indicates to be subjected to the influence of the bubbles and that more the numbers of the bubbles, there is more difference between the obtained values and the true values.

In the preferred embodiments of the invention, it is arranged that the ultrasonic transmitter-receiver 2a and the reflection board 2b be provided with a specific distance in the sample. But the invention is not restricted to this. If the configuration is provided with the ultrasonic transmitter and the ultrasonic receiver, it is possible to obtain the sonic speed according to c=L/T.

As discussed above, even if the multiple receiving wave generated every transmitting wave can be received irregularly or occasionally because of the bubbles, the invention can perform the stable measurement without the influence of the bubbles by judging whether the receiving waves exist or not before the receiving waves are inputted to the phase synchronizing circuit and performing the phase synchronization only for the received signals.

What is claimed is:

1. An ultrasonic speed measuring method for finding the ultrasonic velocity in a sample based on the propagation time of ultrasonic waves transmitted from an ultrasonic transmitter, said waves being propagated between the ultrasonic transmitter and an ultrasonic receiver, said method comprising the steps of:

delaying receiving waves received by the ultrasonic receiver for a specific time;

activating a PLL circuit based on the receiving waves not delayed;

oscillating continuous waves of which the phase is synchronized to the timing of the delayed receiving waves;

preparing the transmittal timing of the ultrasonic waves from the continuous waves: and calculating the ultrasonic velocity in the sample based on the propagation time of the ultrasonic waves.

2. An ultrasonic speed meter for finding the ultrasonic velocity in a sample based on the propagation time of ultrasonic waves transmitted from an ultrasonic transmitter, said waves being propagated between an ultrasonic transmitter and an ultrasonic receiver, said apparatus comprising:

a first delay circuit for delaying the receiving waves received by the ultrasonic receiver for a specific time;

a PLL circuit which is activated based on the receiving waves not delayed and oscillating the continuous waves whose phase is synchronized to the timing of the delayed waves obtained by the first delay circuit a transmitting circuit for transmitting the ultrasonic waves at the timing based on the continuous waves oscillated by the PLL circuit; and calculating means for calculating the ultrasonic velocity in the sample based on the propagation time of the ultrasonic waves.

3. An ultrasonic speed meter according to claim 2, wherein the PLL circuit comprises a gate circuit between the phase comparator and the local oscillator for inputting an output of a phase comparator to a local oscillator when the receiving waves are detected.

4. An ultrasonic speed meter according to claim 2, wherein the PLL circuit further comprises:

a second delay circuit for delaying the output of the local oscillator for the specific time and considering the output as the reference signal of the phase comparator; and the transmitting circuit for oscillating the ultrasonic waves at the timing of the output of the local oscillator.

5. An ultrasonic speed meter according to claim 4, wherein the second delay circuit delays the output of the local oscillator for the specific time necessary for the circuit configuration.

6. An ultrasonic speed meter for finding the ultrasonic velocity in a sample based on the propagation time of ultrasonic waves transmitted from a ultrasonic transmitter, said waves being propagated between an ultrasonic transmitter and an ultrasonic receiver, wherein the ultrasonic receiver generates signals in response to received waves, said apparatus comprising:

a first delay circuit for delaying, for a specific time, signals the ultrasonic receiver generates in response to the received waves;

a PLL circuit which accepts delayed signals from the delay circuit, and also accepts non-delayed signals from the ultrasonic receiver, which PLL circuit is actuated in response to signals from the ultrasonic receiver which are not delayed, and which PLL circuit produces continuous signals whose phase is synchronized to the timing of the delayed signals obtained from the first delay circuit;

a transmitting circuit which receives signals from the PLL circuit and activates the ultrasonic transmitter to produce ultrasonic waves with a timing based on the continuous signals produced by the PLL circuit; and calculating means for calculating the ultrasonic velocity in the sample based on the propagation time of the ultrasonic waves.

* * * * *